US010246672B2

(12) United States Patent
Fountain

(10) Patent No.: US 10,246,672 B2
(45) Date of Patent: *Apr. 2, 2019

(54) NANOLIPIDS WITH ENCAPSULATED ALCOHOL

(71) Applicant: NuVessl, Inc., Calgary (CA)

(72) Inventor: Michael W. Fountain, Tampa, FL (US)

(73) Assignee: NuVessl, Inc., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/673,603

(22) Filed: Aug. 10, 2017

(65) Prior Publication Data

US 2017/0335261 A1 Nov. 23, 2017

Related U.S. Application Data

(60) Division of application No. 15/479,847, filed on Apr. 5, 2017, which is a continuation of application No. 13/840,810, filed on Mar. 15, 2013, which is a continuation-in-part of application No. 12/772,838, filed on May 3, 2010, now Pat. No. 8,545,874, which is a continuation of application No. 11/644,281, filed on Dec. 22, 2006, now Pat. No. 8,597,678.

(60) Provisional application No. 60/755,171, filed on Dec. 30, 2005.

(51) Int. Cl.

| | |
|---|---|
| *A23G 9/32* | (2006.01) |
| *A23G 9/48* | (2006.01) |
| *A61K 9/51* | (2006.01) |
| *C12G 3/00* | (2006.01) |
| *C12G 3/04* | (2006.01) |
| *A23L 33/10* | (2016.01) |
| *A23P 10/35* | (2016.01) |

(52) U.S. Cl.
CPC ............... *C12G 3/00* (2013.01); *A23G 9/32* (2013.01); *A23G 9/48* (2013.01); *A23G 9/485* (2013.01); *A23L 33/10* (2016.08); *A23P 10/35* (2016.08); *A61K 9/51* (2013.01); *A61K 9/5123* (2013.01); *A61K 9/5192* (2013.01); *C12G 3/04* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 3,786,159 A | 1/1974 | Sato et al. | |
| 4,790,999 A | 12/1988 | Ashmont et al. | |
| 4,880,635 A * | 11/1989 | Janoff | A61K 9/1271 424/450 |
| 5,004,611 A | 4/1991 | Leigh | |
| 5,009,819 A | 4/1991 | Popescu et al. | |
| 5,019,414 A | 5/1991 | Valdez | |
| 5,269,979 A * | 12/1993 | Fountain | A01N 25/04 264/4.1 |
| 5,437,274 A | 8/1995 | Khoobehi et al. | |
| 5,498,420 A * | 3/1996 | Mentrup | A61K 8/14 424/401 |
| 5,716,638 A | 2/1998 | Touitou | |
| 5,814,343 A | 9/1998 | Jones et al. | |
| 5,879,703 A | 3/1999 | Fountain | |
| 5,885,921 A | 3/1999 | Krupey | |
| 6,096,331 A | 8/2000 | Desai et al. | |
| 6,203,778 B1 | 3/2001 | Brasch | |
| 6,444,242 B1 | 9/2002 | Skelbaek et al. | |
| 7,981,456 B2 | 7/2011 | Leibovich et al. | |
| 2001/0006643 A1* | 7/2001 | Hope | A61K 9/1278 424/400 |
| 2001/0041208 A1 | 11/2001 | Orris et al. | |
| 2001/0046545 A1 | 11/2001 | Jones | |
| 2004/0253360 A1 | 12/2004 | Squicciarini | |
| 2005/0142253 A1 | 6/2005 | Purcell | |
| 2005/0191330 A1 | 9/2005 | Huglin | |
| 2008/0226777 A1 | 9/2008 | Helfend et al. | |
| 2009/0155427 A1 | 6/2009 | Jobe et al. | |
| 2010/0062134 A1 | 3/2010 | Melvin et al. | |

FOREIGN PATENT DOCUMENTS

| | | |
|---|---|---|
| WO | WO9916426 | 4/1999 |
| WO | WO99001043 | 6/2000 |

OTHER PUBLICATIONS

Scholfield, Journal of the American Oil Chemists Society, 58, 10, 1981 (Year: 1981).*
Godin, B., et al., "Ethosomes: New prospects in Transdermal Delivery," Critical Reviews in Therapeutic Drug Carrier Systems, vol. 20(1), (2003) pp. 63-102.
Gruner, S. et al., "Novel Multilayered Lipid Vesicles: Comparison of Physical Characteristics of Multilamellar Liposomes and Stable Pluilamellar Vesicles," Biochemistry, vol. 24 (1985) pp. 2833-2842.
Guzman, C., et al., "Antibody Responses in the Serum and Respiratory Tract of Mice Following Oral Vaccination with Liposomes Coated with Filamentous Hemagglutinin and Pertussis Toxoid," Infection and Immunity, vol. 61, No. 2, (1993) pp. 573-579.

(Continued)

*Primary Examiner* — Robert A Wax
*Assistant Examiner* — William Craigo
(74) *Attorney, Agent, or Firm* — Hemingway & Hansen, LLP; D. Scott Hemingway

(57) ABSTRACT

A method for preparing ethanol-containing nanolipid particles, which can be used in food products, frozen desserts, or beverages. The method comprises nanolipidic vehicles in which ethanol-containing substances are encapsulated, said ethanol-containing nanolipidic vehicles can be combined with food products, desserts or beverage ingredients including those that are subsequently frozen. The food product, dessert or beverage can remain in a frozen state during consumption by an individual. A composition comprising ethanol-containing nanolipid particles, which can be used in food products, frozen desserts, or beverages.

19 Claims, No Drawings

(56) References Cited

OTHER PUBLICATIONS

International Preliminary Report on Patentability for corresponding Application PCT/US2006/048770; Jan. 29, 2008.

Komatsu, H. et al., "Effects of ethanol on permeability of phosphatidylcholine/cholesterol mixed with liposomal membranes," Chemistry and Physics of Lipids, vol. 85 (1997) pp. 67-74.

Masson, G., "Characterization of Small Lipid Vesicles Prepared by Microfluidization," Progress in Colloid & Polymer Science, vol. 79, (1989) pp. 49-51.

Maurer, N. et al., "Spontaneous entrapment of polynucleotides upon electrostatic interaction with ethanol-destabilized cationic liposomes," Biophysical Journal, vol. 80 (2001) pp. 2310-2326.

Nounou, M. et al., "In vitro release of hydrophilic and hydrophobic drugs from liposomal dispersions and gels." Acta Pharma 56 (2006) pp. 311-324.

Panico, A. et al., "Preparation of liposome formulations containing immunomodulatory peptides." Pharmaceutica Acta Helvetiae 72 (1997) pp. 1-10.

Philippot, J.R., et al., "Liposomes as Tools in Basic Research and Industry." CRC Press, (1995) pp. 7-8.

Schnyder, A., et al., "Drug Transport to Brain with Targeted Liposomes." NeuroRx, vol. 2, No. 1 (2005) pp. 99-107.

Singh, A.K., et al., "Applications of Antibody and Fluorophore-derivatized Liposomes to Heterogeneous Immunoassays for D-dimer" Biotechnology Progress, vol. 12, No. 2 (1996) pp. 272-280.

Zheng, J.Y., et al., "Pulmonary Peptide Delivery: Effect of Taste-Masking Excipients on Leuprolide Suspension Metered-Dose Inhalers," Pharmaceutical Development and Technology, vol. 6(4) (2001) pp. 521-530.

Ghaghada, Ketan, et al., "T1 Relaxivity of Core-encapsulated Gadolinium Liposomal Contrast Agents—Effects of Liposome Size and Internal Gadolinium Concentration," Acad. Radiol. (2008) 15(10), 1259-1263.

Kremer, et al., "Vesicles of Variable Diameter Prepared by Modified Injection Method," Biochemistry 16(1977) pp. 3932-3935.

Pillman et al., "Effects of Ethanol on the Organization of Phosphocholine Lipid Bilayers," J. Phy. Chem B (2010) 114, pp. 3840-3846.

Yang et al., "On the Stability of Liposomal Cantansomes in Aqueous Alcohol Solution," Langmuir (2008) pp. 1695-1700.

Zhao et al., "Size-induced Enhancement of Chemical Exchange Saturation Transfer (CEST) Contrast in Liposomes," J A. Chem Soc (2008) 130, pp. 5178-5184.

Berger, et al., "Filter extrusion of liposomes using different devices: comparisons of liposome size, encapsulation efficiency, and process characteristics," Int J Pharm, vol. 223, n.1-2 (2001), pp. 55-68.

Dos Santos, et al. "pH gradient loading of anthracyclines into cholesterol-free liposomes: enhancing drug loading rates through use of ethanol," Biochemica et Biophysica Acta 1661 (2004), pp. 47-60.

Muller, et al., "Solid lipid nanoparticles (SLN) for controlled drug delivery—a review of the state of the art," EP J of Pharma & Biopharma 50 (2000), pp. 161-177.

* cited by examiner

NANOLIPIDS WITH ENCAPSULATED ALCOHOL

CROSS REFERENCE TO RELATED APPLICATIONS

This application is a divisional of U.S. application Ser. No. 15/479,847 filed Apr. 5, 2017, which is a continuation of U.S. application Ser. No. 13/840,810 filed Mar. 15, 2013, which is a continuation-in-part of U.S. application Ser. No. 12/772,838 filed May 3, 2010, which is a continuation of U.S. application Ser. No. 11/644,281 filed Dec. 22, 2006, and which claims the benefit of U.S. Provisional Application No. 60/755,171 filed Dec. 30, 2005.

STATEMENT REGARDING FEDERALLY SPONSORED RESEARCH OR DEVELOPMENT

Not applicable.

TECHNICAL FIELD OF INVENTION

This invention relates to the field of encapsulation of ethanol in nanolipidic particles.

BACKGROUND OF THE INVENTION

Frozen foods, particularly frozen desserts and frozen beverages, are very popular with consumers. Frozen desserts, such as ice creams and sorbets are consumer favorites, and are frequently flavored with liqueurs such as Grand Marnier® and Kahlua®. Frozen beverages, such as margaritas and piña coladas, are also popular. Attempts to provide such frozen desserts and beverages with an ethanol content comparable to the non-frozen counterparts has been met with limited success due to the substantially lower freezing point of ethanol as compared to water-based products.

The freezing point of pure water is 0° C. (32° F.). The freezing point of pure ethanol is −114° C. (−173.2° F.). The freezing point of ethanol containing products will fall into the range between these two limits, with the freezing point of an alcohol-containing food product depending upon the percentage of alcohol (ethanol) in the final product. Practical and physical limitations prevent the use of commercial freezing mechanisms capable of maintaining high-ethanol content foods at temperatures low enough to stay frozen. Most freezing apparatuses have a functional range for freezing a food product, and consumer safety will also dictate a temperature range wherein frozen foods may be safely ingested. Freezing food products with alcohol ranging up to 15% in the final concentration requires freezing at temperatures substantially below the freezing point of water.

This decreased freezing point has long been understood to a limiting factor in the ability to make products containing ethanol which can remain frozen long enough for an individual to reasonably consume the product while it remains in the frozen state. Various means have been employed to overcome this obstacle, most of which have involved the addition of stabilizing materials, such as gels or agar, to the food product. Even then, there has been limited success.

Incorporating passenger molecules, such as pharmaceutical active ingredients, in lipid vesicles such as liposomes has been reported in the prior art. An amphipathic carrier structure denoted as a Solvent Dilution Microcarrier ("SDMC") was disclosed in U.S. Pat. No. 5,269,979. In general, the '979 patent described making a plurality of SDMC vehicles by solubilizing an amphipathic material and a passenger molecule in a first quantity of a non-aqueous solvent. Following this, a first quantity of water was added, forming a turbid suspension. In a subsequent step, a second quantity of non-aqueous solvent was added to form an optically clear solution. The final step of a preferred embodiment was to organize the optically clear solution into SDMC vehicles by mixing with air or a second quantity of water.

In U.S. Pat. No. 5,879,703, a method for preparing a shelf-stable precursor solution useful for remote encapsulation of active ingredients was described. In '703, the precursor solution was made by solubilizing an amphipathic material in a non-aqueous solvent. A quantity of water was added to the first mixture to form a precursor solution characterized by optical clarity and being monophasic at room temperature. The precursor solution could be stored for an extended period of time—and the desired active ingredient added at a later time, perhaps at a remote location, to form a loaded precursor solution. SDMCs could be formed, in preferred embodiments, from the loaded precursor solution by diluting with water or mixing with air. SDMCs ranged from about 230 to about 412 nanometers in size.

Although SDMCs and the shelf-stable precursor solution provided for making vehicles suitable for delivering active ingredients in a variety of applications, a need remained for improved vehicles for delivery of passenger molecules.

It has now been found that the shelf-stable precursor solution such as described in the '703 patent can be used as a starting material in a novel method which results in vehicles of a smaller size than previously reported. The starting material is manipulated by dilution with a non-aqueous solvent, either before or after loading with a passenger molecule, to provide one or more defined populations of nanolipidic particles ("NLPs") which range in size from about 1 nanometer to about 20 nanometers.

NLP assemblies are formed from the NLPs which range in size from about 30 nanometers to about 200 nanometers. In addition, it has been found that NLPs can be used in a method for making carrier vehicle preparations which are mixed smaller and larger carrier vehicles, or having a larger mean size of about 200-300 nanometers, but improved encapsulation of passenger molecules.

SUMMARY OF THE INVENTION

A means has now been found by which ethanol can be effectively, efficiently and economically encapsulated in a nanolipid particle for possible consumer consumption, such as encapsulation of ethanol maintained at percentages not previously possible for consumer ingestion.

A method for preparing ethanol-containing food products, frozen desserts and beverages is disclosed using alcohol encapsulated in nanolipid particles and assemblies. The method comprises nanolipidic vehicles in which ethanol-containing substances are encapsulated, said ethanol-containing nanolipidic vehicles are combined with dessert or beverage ingredients which can subsequently consumed or incorporated into food products, such as frozen foods, desserts or beverages. These food items can remain in a frozen state during consumption by an individual without losing the characteristics of the alcohol encapsulated in nanolipid particles and assemblies.

The method of the claimed invention provides for the encapsulation of various ethanol-containing substances in lipid-based vesicles, said vesicles being preferably soy-based, which may be added to ingredients appropriate for consumption in a food product, such as a dessert or beverage, and the combination may then be frozen by established means available in food service to produce an ethanol-containing food product or frozen food product capable of maintaining a frozen state at consumer-safe temperatures for a period of time sufficient for consumption of said product. Additional stabilizing materials do not need be added to the food product to achieve this result.

DETAILED DESCRIPTION

Preparation of Nanolipidic Particles (NLPs) and NLP Assembly Populations

Nanolipidic particles (NLPs) are prepared according to the techniques set forth in United States Patent Application Publication No. 2007/0154539 A1, published Jul. 7, 2007, United States Patent Application Publication No. 2010/0239686 A1, published Sep. 23, 2010, and United States Patent Application Publication. No. 2012/00195940 A1, published Aug. 2, 2012, which are both herein incorporated by reference. NLPs are prepared from a Shelf-Stable Precursor Stock, prepared according to U.S. Pat. No. 5,879,703 which is also incorporated by reference as if fully set forth herein.

NLPs are made from a precursor solution as described in U.S. Pat. No. 5,879,703. As stated in the '703 patent, a precursor solution may be made by solubilizing an amphipathic material in a first quantity of a non-aqueous solvent appropriate to solubilize the amphipathic material to form a first mixture. The amphipathic material preferably comprises phospholipids (PL). Preferred phospholipids comprise one or more of the following phosphatides: phosphatidylcholine (PC), phosphatidylethanolamine (PE), phosphatidic acid (PA) and phosphatidylinositol (PI). In a preferred embodiment, PC, PE, PA and PI are combined. A preferred ratio of PLs useful in the invention is PC:PE:PA:PI of 6.5:2.5:0.7:0.3 in ethanol. Preferably, one gram of PL is solubilized in 5.0-7.5 mL of ethanol solvent.

After dissolution of the amphipathic material, a quantity of water is added to form a turbid suspension. The amount of water to add is approximately 9 kg of water to 31 kg of dissolved amphipathic material, but the amount of water can be varied to result in the desired turbid suspension. A second quantity of non-aqueous solvent, such as ethanol, is added until the turbid suspension is monophasic and has optical clarity at room temperature. This resulting product is a precursor solution which is shelf-stable over time.

In the '703 patent, it was disclosed that a precursor solution made according to the process disclosed therein was shelf stable at least up to two years, and perhaps longer, as long as it remains in a monophasic condition. It has been recently determined that precursor solutions made by this method are stable for at least eight years, independent of manufacturing, location, season, year and lot.

It has now been found that a precursor solution such as disclosed in '703 can be used as a starting material to make nanolipidic particles (NLPs) and NLP assemblies. In '703, the precursor solution was disclosed as being useful for making SDMCs (Solvent Dilution Microcarriers) at a later point in time and, perhaps, a remote location. SDMCs have a diameter of from about 230 to about 412 nm. In contrast, NLPs have a mean diameter of from about 1 nm to about 20 nm and NLP assemblies have a mean diameter from about 30 nm to about 200 nm.

Various populations of NLP assemblies may be made for various applications. Preferred populations range from about 40-60 nm; about 60-80 nm; about 80-110 nm, about 110-140 nm, and about 150-200 nm. NLP assembly populations are generally 20-30% smaller in diameter than SDMCs for the same passenger molecule.

A slightly larger population or mixed population of carrier vehicles is referred to herein as ECVs or encapsulating carrier vehicles. Although overlapping the mean diameter of SDMCs, the ECV is made using a different method employing NLPs and the result is a carrier vehicle population which has been found to exhibit a higher encapsulating efficiency. The ECVs are described as having a mean diameter from about 200 nm to 300 nm.

To make carriers for passenger molecules, such as NLP populations, NLP assemblies, or ECVs according to the method disclosed in United States Patent Application Publication Nos. 2007/0154539, 2010/0239686 and 2012/0195940, the precursor solution as previously described in the '703 patent is diluted with a suitable solvent or mixed solvent system which is compatible with the solvent system used in the precursor solution. The concentration of solvent in the NLPs is from about 0.5% to about 14% by volume. This dilution is performed either before or after addition of the passenger molecule as will be further described in detail below.

For the present invention, NLPs are prepared by first mixing an aliquot of the aforementioned shelf-stable precursor stock solution with varying amounts of ethanol to produce NLPs having specific size ranges. These NLPs are then diluted with distilled water to achieve the final ethanol concentration for the claimed composition. Further, these NLPs can be used to form NLP assemblies and carrier vehicle populations utilizing mixed NLP sizes and increased encapsulation of passenger molecules.

The following calculation is used to provide data for the table below:

Neat or Control: (85.0% ethanol in precursor stock)×(1 ml of preparation)/20 ml of distilled water=4.3% ethanol $$\frac{85.0\% \text{ EtOH}}{100 \text{ mL precursor stock}} \times \frac{1 \text{ mL precursor stock}}{20 \text{ mL total volume}} =$$

% EtOH in *NLP* preparation

The resulting sizes and relative ethanol concentrations of the finished preparations are tabulated below.

NLPs sizes of 1-20 nm and 10-12 nm are made according to paragraph [0007] of the specification United States Patent Application Publication No. 2007/0154539 by dilution of the precursor solution with a non-aqueous solvent.

In Example 1, Table 1 of United States Patent Application Publication No. 2007/0154539, the following precursor/ethanol ratios yield NLP assembly populations. The resulting ethanol concentration of the final product has been added to the Table provided in the specification at Paragraph [0035] to demonstrate the much lower concentration of ethanol in the NLP assembly populations. Resulting ethanol concentrations were determined by adding the ethanol concentration for 1 mL of precursor stock (0.85 mL EtOH/1 mL solution) to the additional amount of ethanol per the chart below and determining the amount of EtOH per mL of the resulting solution, then dividing by the 20 mL water added to make the final solution. [For example—0.85 mL EtOH/1 mL stock+2.0 mL EtOH added=2.85 mL EtOH/3 mL total solution→0.95 mL EtOH/1 mL×1 mL/20 mL diH$_2$O× 100=4.75% final EtOH concentration for a 110 nm size NLP population]

| Stock Precursor Solution | Ethanol added | No Passenger | Size | Resulting Ethanol Concentration |
|---|---|---|---|---|
| 1 mL | 0 mL | [Control} | 278 nm | 4.3% |
| 1 mL | 0.2 mL | [Mixed population] | 242 nm | 4.35% |
| 1 mL | 0.5 mL | [NLP Assembly] | 186 nm | 4.4% |
| 1 mL | 0.8 mL | [NLP Assembly] | 160 nm | 4.5% |
| 1 mL | 1.0 mL | [NLP Assembly] | 138 nm | 4.6% |
| 1 mL | 2.0 mL | [NLP Assembly] | 110 nm | 4.75% |
| 1 mL | 3.0 mL | [NLP Assembly] | 98 nm | 4.8% |
| 1 mL | 5.0 mL | [NLP Assembly] | 61 nm | 4.85% |
| 1 mL | 10.0 mL | [NLP Assembly] | 34 nm | 4.9% |

As evidenced by this example, the ethanol concentration is less than 5% for each of the preparations. Similar ethanol concentrations are also produced with the preparations in Examples 2, 3, 4, 5, 6 & 8. The remaining examples from the specification have slightly different ethanol concentrations as reported in the sections below.

In Example 7 of United States Patent Application Publication No. 2007/0154539, the taste of NaCl is masked by encapsulation in an NLP preparation. The final ethanol concentration in the NLPs for this example is less than 1%. For this preparation, 1 mL of NLP stock solution is diluted into 100 mL distilled water with a resulting concentration of 0.9% [(85 mL EtOH/100 mL NLP stock×1 mL/101 mL total solution)×100=0.9%]

In Example 9 of United States Patent Application Publication No. 2007/0154539, caffeine is the passenger molecule for an NLP preparation with an ethanol concentration of 14%. For this preparation, 20 mL of NLP stock solution is diluted in 100 mL of distilled water with a resulting ethanol concentration of 14%. [(85 mL EtOH/100 mL NLP stock×20 mL/120 mL total solution)×100=14%]

In Example 10 of United States Patent Application Publication No. 2007/0154539, production of a preloaded NLP preparation containing caffeine is described. For this preparation, 30 mL of NLP stock solution is diluted in 50 mL of distilled water with a resulting ethanol concentration of 0.5%. [(85 mL EtOH/100 mL NLP stock×30 mL/80 mL total solution)/62.5×100=0.5%]

Example 11 of United States Patent Application Publication No. 2007/0154539 describes the production of preloaded NLP preparations containing lipid soluble vitamins. For this preparation, 1 mL of NLP stock solution is diluted in 50 mL of distilled water with a resulting ethanol concentration of 1.7%. [85 mL EtOH/100 mL NLP stock×1 mL/51 mL total solution)×100=1.7%]

The range of ethanol concentrations for the NLPs of the invention of United States Patent Application Publication No. 2007/0154539 range from a low of about 0.5% as seen in Example 10 to a high of about 14% as seen in Example 9.

The solvent is selected for biocompatibility if the end use of the carriers will require that characteristic. The solvent or mixed solvent system used for dilution must be miscible with the solvents in the precursor solution and should be effective to disperse rather than dissolve the carriers. Most preferably, the solvent used for dilution is ethanol, since it possesses the desired qualities. Ethanol is the solvent of choice for any end use wherein the particles are for ingestion. The dilution is preferably conducted in a sequential or serial manner. For example, a first dilution of 1:10 provides a population of carriers, and further serial dilution to about 1:0.5 provides a series of populations of carriers.

The size of the carriers in each dilution can be determined by laser light scattering. Mixed populations of NLPs and larger vesicles may be created at lower dilutions with the non-aqueous solvent. An appropriate instrument for this purpose is the Zetasizer 1000 manufactured by Malvern Instruments, (Worcestershire United Kingdom). Diameters of particles reported herein were determining using the Multimodal Analysis Mode of the Zetasizer 1000 to determine particle size by peak intensities. Other techniques may be used to analyze particle size, which results can be correlated to the numerical values obtained with the light scattering technique described herein.

Addition of the desired passenger molecule occurs prior to dilution with the solvent if the passenger molecule is lipophilic or amphipathic. Addition occurs after dilution if the passenger molecule is water soluble.

Thus, in the case of a lipophilic or amphipathic passenger molecule, the NLP loaded populations form upon dilution with the solvent. NLP assembly populations or ECVs are formed by dilution of the NLP loaded population into water.

In the case of a water soluble passenger molecule, the precursor solution is mixed with a passenger molecule dissolved in water. NLP assembly populations or ECVs are formed upon dilution with the non-aqueous solvent. If a serial dilution technique is used, distinct populations are formed.

Based on curves observed from different classes of compounds, ranges for the finished NLP assembly population can be established for each NLP population used to form the final NLP assembly population. The more non-aqueous solvent that is used to dilute the NLPs, the smaller the NLP assembly populations.

Various NLP loaded populations may be mixed and matched to provide a multifunctional NLP assembly product. The different NLP loaded populations within the NLP assembly could provide a preparation which allows one active ingredient to be preferentially absorbed over the other, thus allowing a control of the rates of release of different ingredients in a single preparation. Alternatively, a single NLP population could be loaded with more than one passenger molecule to provide the multifunctionality.

Another advantage to the NLP technology is that an optically clear solution containing NLPs loaded with passenger molecules can be made by selecting conditions where the NLPs are less than about 150 nm in size. It is many times important that a product appear optically clear or it will fail to gain consumer acceptance. For example, loaded NLPs in an optically clear solution have application in the beverage industry and the pharmaceutical industry for liquid products. As one example, a mouthwash can be prepared that contains NLPs which encapsulates an ingredient for time-release in the mouth. A consumer prefers to purchase an optically clear mouthwash rather than a cloudy one.

The passenger molecules suitable for use in forming a NLP loaded population are numerous. In one embodiment, passenger molecules can be selected which exhibit lipid solubility or are amphipathic. These molecules have solubility profiles ideally suited for loading into NLPS. In another embodiment, water soluble molecules may be incorporated into NLPs by solubilization into the aqueous solution used to form the finished NLP product. Using these two approaches virtually any molecule may be incorporated as a passenger molecule into NLP products of defined sizes. An innovative use of both approaches may be used to incorporate both lipid and water soluble compounds into a NLP assembly product by first incorporating lipid soluble compounds into NLPs prior to dilution with ethanol and second incorporating water soluble molecule(s) into the water solution used to form the finished NLP product of defined size.

NLPs may also be used in the food and beverage industry. For example, NLPs incorporating caffeine may be used in dietary supplements for appetite suppression. Encapsulation in NLPs has been found to be effective to mask the taste of the passenger molecule if it is desired that tasting of such be bypassed upon ingestion.

Another application in the food and beverage industry is the incorporation of substances into NLPs which will be tasted, rather than masked. Flavorings such as peppermint oil and other oils are appropriately incorporated into NLPs. The encapsulation of oil-containing substances may lead to increased shelf life in that the encapsulated substance is protected from oxidation. In addition, the encapsulation of substances would permit additional options for manufacturers and consumers.

As just one example, a manufacturer of a beverage could prepare and bottle one base flavor. The consumer would then have the option of adding NLP packets to the beverage to meet the taste preferences of the consumer or to enrich it with vitamins. A consumer that prefers a strong peppermint flavoring in a chocolate drink could add NLPs containing peppermint oil to his or her beverage. Substances that are meant to be tasted can also be loosely associated with the exterior of the NLP by providing such substances in the aqueous phase of the procedure. For example, an NLP containing a vitamin that preferably should not be tasted can have a pleasant taste on the outside thereof.

If it is desired that the NLPs remain in the mouth so that their contents can be tasted, a natural carbohydrate or sugar can be linked to the NLP by merely providing it in the aqueous solution. This will stick to the inside of the mouth for a period of time, and normal mouth chemistry and mastication will release the contents of the NLPs to provide the desired effect. The NLPs can also be subjected to agitation and shear such as in a blender or heavy industrial equipment at a manufacturing site to provide flavorings to foods and beverages.

If the desired passenger molecule is water soluble, the passenger molecule should first be dissolved in water. The incorporation step, or loading of the passenger molecule into the NLP, is accomplished when the NLP product is formed by adding the dissolved passenger molecule to the precursor solution.

The nanolipidic particles with encapsulated ethanol of the invention have a softer "mouth feel" than a preparation containing free ethanol. The encapsulation process leads to the ethanol being sequestered inside the nanolipid such that the ethanol does not immediately contact the mucosa in the mouth. Other passenger molecules which may in the preparation, such as vitamins and pharmaceutical substances, are similarly sequestered within the nanolipidic particles.

Sample Preparation of NLPs and NLP Assembly Populations with Encapsulated Ethanol-Containing Substances NLPs encapsulating ethanol-containing substances were prepared as follows:

Solvent-diluted precursor stock was prepared by adding 1 part shelf-stable precursor stock to 0.3 part ethanol to form a solvent-diluted precursor.

An ethanol-containing substance having an ethanol content of 0.2%-50% by volume is dissolved in an aqueous solvent to form an aqueous-ethanol monophase. Ethanol-containing substances suitable for encapsulation include vodka, gin, rum, bourbon, grain alcohols, or liqueurs containing vodka, gin, rum, bourbon, or grain alcohols.

An aliquot of solvent-diluted precursor stock added to an aliquot of the aqueous-ethanol monophase. This solution is stirred at room temperature resulting in a loaded NLP population with the desired ethanol-containing substance encapsulated within the nanolipid particles to yield a liposomal concentrate comprising ethanol in the amount of about 0.1% to 15.0% by volume.

The size of the loaded NLPs may be determined by using the Malvern 1000 Zetasizer Laser Light Scattering Instrument set to analyze populations using multimodal analysis mode. The size of the finished preparation was determined to be 20 nm-150 nm.

Nanolipid particle sizes useful for the preparation of the invention can be increased or decreased by adjusting the ratio of ethanol to Solvent Dilution Microcarrier (SDMC) used in preparation of the precursor stock solution. Particle sizes can range from approximately 60 nm using 20 parts ethanol: 1 part SDMC up to 170 nm using 0.3 part ethanol: 1 part SDMC. Sizes of NLP and NLP assembly populations useful for the method of the invention are 20 nm to 300 nm, preferably 20 nm to 170 nm.

One or more additional dilutions of the precursor solution may be made with ethanol solvent in order to provide a desired size of NLPs and number of NLPs per unit volume. The more ethanol solvent that is used to dilute the NLPs, the smaller the resulting NLP assembly populations will be.

In one embodiment, nanolipid particles having ethanol encapsulated at a concentration of 5.0%-8.0% by volume, is added to base ingredients for gelato. This gelato mixture is then frozen by a commercially acceptable process to produce a frozen gelato for consumption.

EXAMPLE 1

Frozen alcohol-containing gelatos having a final ethanol concentration up to 0.2%-15.0% by volume which have been prepared by the claimed method of the invention include the following:

| Gelato Flavor | % Alcohol by volume |
| --- | --- |
| Raspberry Cream | 8.0% |
| Orange Cream (Grand Marnier ™) | 8.0% |
| Bourbon Vanilla | 5.0% |

In another embodiment, nanolipidic particles having ethanol encapsulated at a concentration of 5.0% by volume are added to base ingredients for a sorbet or frozen beverage. This sorbet or frozen beverage mixture is then frozen by a commercially acceptable process to produce a frozen sorbet, pops, or beverage for consumption. Ice pops and other frozen products of a similar nature can be prepared by the same method.

EXAMPLE 2

Frozen alcohol-containing sorbets, pops, and beverages having a final ethanol concentration up to 0.2%-15.0% by volume can be been prepared by the claimed method of the invention include the following:

| Sorbet or Beverage Flavor | % Alcohol by volume |
| --- | --- |
| Piña Colada | 5.0% |
| Mojito | 5.0% |
| Strawberry Margarita | 5.0% |
| Apple Martini | 5.0% |

In yet another embodiment, nanolipid particles having ethanol encapsulated at a concentration of up to 15.0% by volume is added to base ingredients for a syrup or topping for a frozen dessert.

EXAMPLE 3

Alcohol-containing syrups and toppings having a final ethanol concentration up to 0.2%-15.0% by volume for frozen desserts which have been prepared by the claimed method of the invention include the following:

| Syrup or Topping Flavor | % Alcohol by volume |
|---|---|
| Caffe (Kahlua ®) | 15.0% |
| Chocolate Mint | 15.0% |
| Caramel | 15.0% |
| Raspberry | 15.0% |
| Grand Marnier ® | 15.0% |
| Limoncello | 15.0% |

Stability of NLPs in Commercially Available Alcoholic Beverage Products

NLPs (1:10 Precursor to Ethanol, volume/volume) were prepared and diluted 1:10 (NLP volume/volume) in commercially available alcoholic beverage products and stored for one week at Room Temperature. After one week the mixtures were vortexed, diluted 1:10 (volume/volume) in distilled water, and the size of the NLPs were analyzed using a Zetasizer 1000 (Malvern Instruments). The results of the stability study were as follows:

| Citron ® Vodka | 1:10 NLP | 150 nm |
|---|---|---|
| Malibu ® Coconut Rum | 1:10 NLP | 130 nm |
| Beefeater ® Gin | 1:10 NLP | 150 nm |

Stability of NLPs in 100 Proof (50% Volume/Volume in Distilled Water) Ethanol Mixtures NLPs (1:10 and 1:20 Precursor to Ethanol, volume/volume) were prepared and diluted 1:10 in 100 proof mixtures of ethanol and water (50% ethanol, volume/volume). The samples were placed in a commercial freezer for 14 days, removed, allowed to thaw and warm to Room Temperature. Both samples were homogenous and optically clear, without any precipitation. The samples were vortexed and the size of the NLPs were determined using a Zetasizer 1000 (Malvern Instruments). The results of the analyses were:
100 Proof Ethanol in Distilled Water Containing NLPs

| 1:10 NLP | 163 nm |
|---|---|
| 1:20 NLP | 142 nm |

Stability of NLPs after Repeated Freeze Thaw Stored in 25 Proof Ethanol in Distilled Water NLPs (1:5, 1:10 and 1:20 Precursor to Ethanol volume/volume) were prepared and added 1:10 (volume/volume) into solutions of 25 Proof Ethanol in Distilled Water (12.5% Ethanol in Distilled Water, volume/volume). All mixtures were optically clear. The initial size of the NLPs and subsequent size analyses conducted On days 7, 14 and 21 were performed using a Zetasizer 1000 (Malvern Instruments). After the initial size determinations the samples were placed into a commercial freezer for intervals of 7 days. On days 7, 14 and 21 the samples were removed from the freezer allowed to thaw and warm to Room Temperature.

They were vortexed and subjected to size analyses after which they were returned to the commercial freezer. At days 7, 14 and 21 all preparations after equilibrating to Room Temperature were optically clear and free of any precipitation. The results of the size analyses were:

| NLP | Time 0 | 7 Days | 14 Days | 21 Days |
|---|---|---|---|---|
| 1:5 | 156 nm | 160 nm | 167 nm | 162 nm |
| 1:10 | 77 nm | 82 nm | 92 nm | 94 nm |
| 1:20 | 105 nm | 100 nm | 106 nm | 116 nm |

The NLPs and NLP assembly populations can also be used to formulate a delivery vehicle for pharmaceuticals, such as analgesics, as an admixed passenger with the NLPs with encapsulated ethanol. The admixed passenger loaded NLPs can then be mixed with ingredients suitable for making a frozen food product. The loaded NLP-frozen food ingredient mixture can be frozen in a form such as an ice pop to provide a delivery vehicle for the encapsulated ingredients. One practical application of such a delivery device would be in the treatment of sore throats in individuals.

The invention can be characterized as follows: a method for making nanolipid particles (NLPs) having ethanol encapsulated within said nanolipidic particles, comprising the steps of: a) providing a precursor solution; b) diluting said precursor solution with an ethanol solvent to produce a solvent-diluted precursor solution; c) adding an ethanol-containing substance having an ethanol content of 0.2%-50.0% by volume to an aqueous solvent to produce an aqueous-ethanol monophase; and c) mixing said solvent-diluted precursor solution with said aqueous-ethanol monophase wherein said mixing produces one or more populations of ethanol-loaded NLPs or NLP assemblies.

The above invention can also be supplemented as follows: (1) wherein said precursor solution is a monophasic optically-clear solution; (2) wherein, said diluting of said precursor solution with said ethanol solvent is at a ratio ranging from about 1 part precursor to about 20 parts solvent to a ratio ranging from about 1 part precursor to about 0.3 parts solvent; (3) wherein said NLP assembly has a population formed having a mean particle diameter from about 20 nm-300 nm; (4) wherein the concentration of said solvent in said NLPs is from about 0.5% to about 14% by volume; (5) wherein the said concentration of ethanol encapsulated within the nanolipidic particles is from about 0.1% to 15.0% by volume; (6) wherein said diluting of said precursor solution with said ethanol solvent is at a ratio ranging from about 1 part precursor to about 20 parts solvent to a ratio ranging from about 1 part precursor to about 0.3 parts solvent; and; wherein said NLP assembly population is formed having a mean particle diameter from about 20-300 nm; and wherein the concentration of said solvent in said NLPs is from about 0.5% to about 14% by volume, and wherein the said concentration of ethanol encapsulated within the nanolipidic particles is from about 0.1 to 15.0% by volume; (7) wherein said ethanol-containing substance is selected from the group comprising vodka, gin, rum, bourbon, grain alcohol, and liqueurs containing vodka, gin, rum, bourbon, or grain alcohol; (8) wherein the concentration of ethanol in a frozen food product containing ethanol-loaded NLPs is from about 0.1% to 15.0% by volume; (9) wherein said nanolipidic particles with said encapsulated ethanol-containing substance is combined with ingredients suitable for consumption in a frozen food product, and the mixture is frozen at an appropriate temperature such that an ethanol-containing frozen food results; (10) wherein said ethanol-containing frozen food remains in the frozen state for a period of time sufficient for an individual to consume said frozen food; (11) wherein said diluting of said precursor solution with said ethanol solvent is at a ratio of about 1 part precursor to about 10 parts solvent to about 1 part loaded nanolipidic population to about 0.5 parts solvent; (12) wherein the stability of said ethanol-encapsulated nanolipidic particles is such that said particles will maintain structural integrity through multiple freeze-thaw cycles; (13) wherein said precursor solution comprises phospholipids selected from the group consisting of phosphatidylcholine (PC), phosphatidylethanolamine (PE), phosphatidic acid (PA) and phosphatidylinositol (PI) and mixtures thereof; (14) comprising making one or more additional serial dilutions of said precursor solution with said ethanol solvent, wherein said additional dilutions form distinct populations of nanolipidic particles, and wherein said nanolipidic particle populations decrease in size as ethanol concentration in precursor solution increases; (15) comprising making one or more additional dilutions of said precursor solution with said ethanol solvent in order to provide a desired number of nanolipidic particles per unit volume; (16) wherein said aqueous solvent further comprises an additional water-soluble passenger molecule; (17) wherein one or more lipophilic or amphipathic passenger molecules are added to said precursor solution to form a loaded nanolipidic particle population, wherein said nanolipidic particles encapsulate admixed passenger molecules; (18) wherein said frozen food is a frozen beverage or dessert having a final ethanol concentration up to 0.2%-15.0% by volume; (19) wherein said nanolipidic particles with said encapsulated ethanol-containing substance is in a topping for a frozen dessert, said topping having a final ethanol concentration of 0.2%-15.0% by volume; and (20) wherein said nanolipidic particles with encapsulated ethanol are admixed with nanolipidic particles encapsulating a pharmaceutical product, said admixture is added to ingredients suitable for a frozen food, wherein said frozen mixture is a delivery device for said pharmaceutical.

The invention can alternatively be characterized as follows: a composition with nanolipidic particles having alcohol-encapsulated within, comprising: a precursor solution, an ethanol solvent that dilutes said precursor solution and forms a solvent-diluted precursor solution; an ethanol-containing substance having an ethanol concentration of 0.2%-50.0% by volume; an aqueous solvent added to the ethanol-containing substance to produce an aqueous-ethanol monophase; alcohol encapsulated nanolipid particles formed by the mixture of said solvent-diluted precursor solution with said aqueous-ethanol monophase.

This characterization can be supplemented as follows: (1) wherein said precursor solution is a monophasic optically-clear solution; (2) wherein said precursor solution with said ethanol solvent is at a ratio ranging from about 1 part precursor to about 20 parts solvent to a ratio ranging from about 1 part precursor to about 0.3 parts solvent: (3) wherein said NLP assembly has a population formed having a mean particle diameter from about 20 nm-300 nm; (4) wherein the concentration of said solvent in said NLPs is from about 0.5% to about 14% by volume; (5) wherein the said concentration of ethanol encapsulated within the nanolipidic particles is from about 0.2% to 15.0% by volume; (6) wherein said precursor solution with said ethanol solvent is at a ratio ranging from about 1 part precursor to about 20 parts solvent to a ratio ranging from about 1 part precursor to about 0.3 parts solvent; and wherein said NLP assembly population is formed having a mean particle diameter from about 20 nm-300 nm; and wherein the concentration of said solvent in said NLPs is from about 0.5% to about 14% by volume, and wherein the said concentration of ethanol encapsulated within the nanolipidic particles is from about 0.2% to 15.0% by volume; (7) wherein said ethanol-containing substance is selected from the group comprising vodka, gin, rum, bourbon, grain alcohols, and liqueurs containing vodka, gin, rum, bourbon, or grain alcohols; (8) wherein the concentration of ethanol-containing substance in a frozen food product is from about 0.2% to 15.0% by volume; (9) wherein said nanolipidic particles with said encapsulated ethanol-containing substance are combined with ingredients suitable for consumption in a frozen food product, and the mixture is frozen at an appropriate temperature such that an ethanol-containing frozen food results; (10) wherein said ethanol-containing frozen food remains in the frozen state for a period of time sufficient for an individual to consume said frozen food; (11) wherein said precursor solution with said ethanol solvent is at a ratio of about 1 part precursor to about 10 parts solvent to about 1 part loaded nanolipidic population to about 0.5 parts solvent; (12) wherein the stability of said ethanol-encapsulated nanolipidic particles that said particles will maintain structural integrity through multiple freeze-thaw cycles; (13) wherein said precursor solution comprises phospholipids selected from the group consisting of phosphatidylcholine (PC), phosphatidylethanolamine (PE), phosphatidic acid (PA) and phosphatidylinositol (PI) and mixtures thereof; (14) further comprising one or more additional serial dilutions of said precursor solution, wherein said additional dilutions form distinct populations of nanolipidic particles, and wherein said nanolipidic particle populations decrease in size as ethanol concentration in precursor solution increases; (15) further comprising one or more additional dilutions of said precursor solution with said ethanol solvent in order to provide a desired number of nanolipidic particles per unit volume; (16) wherein said aqueous solvent has an additional water-soluble passenger molecule; (17) further comprising one or more lipophilic or amphipathic passenger molecules added to said precursor solution to form a loaded nanolipidic particle population wherein said nanolipidic particles encapsulate admixed passenger molecules; (18) wherein said nanolipid particles are added to a frozen beverage or dessert having a final ethanol concentration from 0.1%-15.0% by volume; (19) wherein said nanolipid particles are added to a food product, said food product having a final ethanol concentration of from 0.1-15.0% by volume; (20) wherein the ethanol encapsulated in said nanolipidic particles is in a concentration of 0.1% to 15.0%; (21) wherein said nanolipidic particles with encapsulated ethanol are admixed with nanolipidic particles encapsulating a pharmaceutical product, said admixture is added to ingredients suitable for a frozen food, wherein said frozen mixture is a delivery device for said pharmaceutical.

A third characterization of the present invention is a follows: a nanolipidic particle (NLP) having encapsulated ethanol, made by a process comprising the steps of: a) providing a precursor solution; b) diluting said precursor solution with an ethanol solvent to produce a solvent-diluted precursor solution; c) adding an ethanol-containing substance having an ethanol content of 0.2%-50.0% by volume to an aqueous solvent to produce an aqueous-ethanol monophase; and c) mixing said solvent-diluted precursor solution with said aqueous-ethanol monophase wherein said mixing produces one or more populations of ethanol-loaded nanolipids (NLPs) or NLP assemblies.

The third characterization can be supplemented as follows: (1) wherein said precursor solution is a monophasic optically-clear solution; (2) wherein said diluting of said precursor solution with said ethanol solvent is at a ratio ranging from about 1 part precursor to about 20 parts solvent to a ratio ranging from about 1 part precursor to about 0.3 parts solvent; (3) wherein said NLP assembly has a population formed having a mean particle diameter from about 20 nm-300 nm; (4) wherein the concentration of said solvent in said NLPs is from about 0.5% to about 14% by volume; (5) wherein the said concentration of ethanol encapsulated within the nanolipidic particles is from about 0.1% to 15.0% by volume; (6) wherein said diluting of said precursor solution with said ethanol solvent is at a ratio ranging from about 1 part precursor to about 20 parts solvent to a ratio ranging from about 1 part precursor to about 0.3 parts solvent; and; wherein said NLP assembly population is formed having a mean particle diameter from about 20 nm-300 nm; and wherein the concentration of said solvent in said NLPs is from about 0.5% to about 14% by volume, and wherein the said concentration of ethanol encapsulated within the nanolipidic particles is from about 0.1% to 15.0% by volume; (7) wherein said ethanol-containing substance is selected from the group comprising vodka, gin, rum, bourbon, grain alcohol, and liqueurs containing vodka, gin, rum, bourbon, or grain alcohol; (8) wherein the concentration of ethanol in said ethanol-loaded NLPs is from about 0.1% to 15.0% by volume; (9) wherein said nanolipidic particles encapsulated with said ethanol-containing substance are combined with ingredients suitable for consumption in a frozen food product, and the mixture is frozen at an appropriate temperature such that an ethanol-containing frozen food results; (10) wherein said ethanol-containing frozen food remains in the frozen state for a period of time sufficient for an individual to consume said frozen food; (11) wherein said diluting of said precursor solution with said ethanol solvent is at a ratio of about 1 part precursor to about 10 parts solvent to about 1 part loaded nanolipidic population to about 0.5 parts solvent; (12) wherein the stability of said ethanol-loaded nanolipids is such that said ethanol-loaded nanolipids will maintain structural integrity through multiple freeze-thaw cycles; (13) wherein said precursor solution comprises phospholipids selected from the group consisting of phosphatidylcholine (PC), phosphatidylethanolamine (PE), phosphatidic acid (PA) and phosphatidylinositol (PI) and mixtures thereof; (14) comprising making one or more additional serial dilutions of said precursor solution with said ethanol solvent, wherein said additional dilutions form distinct populations of nanolipidic particles, and wherein said nanolipidic particle populations decrease in size as ethanol concentration in precursor solution increases; (15) comprising making one or more additional dilutions of said precursor solution with said ethanol solvent in order to provide a desired number of nanolipidic particles per unit volume; (16) wherein said aqueous solvent further comprises an additional water-soluble passenger molecule; (17) wherein one or more lipophilic or amphipathic passenger molecules are added to said precursor solution to form a loaded nanolipidic particle population wherein said nanolipidic particles encapsulate admixed passenger molecules; (18) wherein said frozen food is a frozen beverage or dessert having a final ethanol concentration of 0.1% to 15.0% by volume; (19) wherein said nanolipidic particles with encapsulated ethanol are in a topping for a frozen dessert, said topping having a final ethanol concentration of up to of 0.1% to 15.0% by volume; (20) wherein said nanolipidic particles with encapsulated ethanol are admixed with nanolipidic particles encapsulating a pharmaceutical product, said admixture is added to ingredients suitable for a frozen food, wherein said frozen mixture is a delivery device for said pharmaceutical.

The examples of ethanol encapsulation in NLPs and NLP assemblies presented herein are representative examples only. The method of the invention is applicable to other types of ethanol containing substances and these examples are not meant to constitute the entire range of ethanol-containing substances that may be used in the method disclosed herein.

I claim:

1. An ethanol-loaded nanolipid particle (NLP) carrier made by a process comprising the steps of:
   a) providing a monophasic optically clear precursor stock having phospholipids solubilized in ethanol and water;
   b) diluting said precursor stock with an ethanol solvent to produce a solvent-diluted precursor stock, wherein said diluting of said precursor stock with said ethanol solvent is at a ratio ranging from about 1 part precursor stock to about 20 parts ethanol solvent (volume/volume) to a ratio ranging from about 1 part precursor stock to about 0.3 parts ethanol solvent (volume/volume), said diluting of said precursor stock resulting in one or more substantially unloaded nanolipid particle (NLP), wherein the more ethanol solvent used for said diluting of the precursor stock, the smaller the nanolipids particles will be;
   c) adding an ethanol-containing substance suitable for human consumption to an aqueous solvent to produce an aqueous-ethanol monophase; and
   d) combining said solvent-diluted precursor stock formed in step (b) with said aqueous-ethanol monophase from step (c), wherein said one or more substantially unloaded nanolipid particle (NLP) formed in step (b) becomes loaded with the ethanol-containing substance from step (c) as a passenger in the nanolipid particle (NLP) resulting in one or more ethanol-loaded NLP carrier sized from 20 nm to 300 nm.

2. The nanolipid particle (NLP) carrier of claim 1, wherein said ethanol-containing substance suitable for human consumption is an ethanol-containing beverage product.

3. The nanolipid particle (NLP) carrier of claim 1, wherein, said aqueous-ethanol monophase comprises from 12.5% ethanol in water (volume/volume) to 50% ethanol in water (volume/volume).

4. The nanolipid particle (NLP) carrier of claim 3, wherein said aqueous-ethanol monophase comprises from 15% ethanol in water (volume/volume) to 35% ethanol in water (volume/volume).

5. The nanolipid particle (NLP) carrier of claim 1, wherein said precursor stock comprises phospholipids selected from the group consisting of phosphatidylcholine (PC), phosphatidylethanolamine (PE), phosphatidic acid (PA), phosphatidylinositol (PI), and mixtures thereof.

6. The nanolipid particle (NLP) carrier of claim 1, wherein one or more lipophilic or amphipathic passenger molecules are added to the precursor stock prior to dilution with said ethanol solvent in step (b).

7. The nanolipid particle (NLP) carrier of claim 1, wherein an additional water-soluble passenger molecule is added to the aqueous solvent prior to adding the ethanol-containing substance.

8. The nanolipid particle (NLP) carrier of claim 1, wherein said ethanol loaded NLP carriers formed by combining said solvent-diluted precursor stock with said aqueous-ethanol monophase remain stably sized when frozen by a commercially acceptable process for consumption while frozen.

9. An ethanol-loaded nanolipid particle (NLP) carrier made by a process comprising the steps of:
   a) providing a monophasic optically clear precursor stock having phospholipids solubilized in ethanol and water;
   b) diluting said precursor stock with an ethanol solvent to produce a solvent-diluted precursor stock, wherein said diluting of said precursor stock with said ethanol solvent is at a ratio ranging from about 1 part precursor stock to about 20 parts ethanol solvent (volume/volume) to a ratio ranging from about 1 part precursor stock to about 0.3 parts ethanol solvent (volume/volume), said diluting of said precursor stock resulting in one or more substantially unloaded nanolipid particle (NLP), wherein the more ethanol solvent used for said diluting of the precursor stock, the smaller the nanolipid particles will be;
   c) adding an ethanol-containing substance for human consumption to an aqueous solvent to produce an aqueous-ethanol monophase, said aqueous-ethanol monophase comprising from 12.5% ethanol in water (volume/volume) to 50% ethanol in water (volume/volume); and
   d) combining said solvent-diluted precursor stock formed in step (b) with said aqueous-ethanol monophase from step (c), wherein said one or more substantially unloaded nanolipid particle (NLP) formed in step (b) becomes loaded with the ethanol-containing substance from step (c) as a passenger in the nanolipid particle (NLP).

10. The nanolipid particle (NLP) carrier of claim 9, wherein said ethanol-loaded nanolipid particle (NLP) carriers are sized from 20 nm-300 nm.

11. The nanolipid particle (NLP) carrier of claim 9, wherein said ethanol loaded NLP carriers formed by combining said solvent-diluted precursor stock with said aqueous-ethanol monophase remain stably sized when frozen by a commercially acceptable process for consumption while frozen.

12. The nanolipid particle (NLP) carrier of claim 9, wherein one or more lipophilic or amphipathic passenger molecules are added to the precursor stock prior to dilution with said ethanol solvent in step (b).

13. The nanolipid particle (NLP) carrier of claim 9, wherein an additional water-soluble passenger molecule is added to the aqueous solvent.

14. The nanolipid particle (NLP) carrier of claim 9, wherein said precursor stock comprises phospholipids selected from the group consisting of phosphatidylcholine (PC), phosphatidylethanolamine (PE), phosphatidic acid (PA), phosphatidylinositol (PI), and mixtures thereof.

15. An ethanol-loaded nanolipid particle (NLP) carrier made by a process comprising the steps of:
   a) providing a monophasic optically clear precursor stock having phospholipids solubilized in ethanol and water;
   b) diluting said precursor stock with an ethanol solvent to produce a solvent-diluted precursor stock, wherein said diluting of said precursor stock with said ethanol solvent is at a ratio ranging from about 1 part precursor stock to about 20 parts ethanol solvent (volume/volume) to a ratio ranging from about 1 part precursor stock to about 0.3 parts ethanol solvent (volume/volume), said diluting of said precursor stock resulting in one or more substantially unloaded nanolipid particle (NLP), wherein the more ethanol solvent used for said diluting of the precursor stock, the smaller the nanolipid particles will be;
   c) adding an ethanol-containing substance for human consumption to an aqueous solvent to produce an aqueous-ethanol monophase, said aqueous-ethanol monophase comprising from 15% ethanol in water (volume/volume) to 35% ethanol in water (volume/volume); and
   d) combining said solvent-diluted precursor stock formed in step (b) with said aqueous-ethanol monophase from step (c), wherein said one or more substantially unloaded nanolipid particle (NLP) formed in step (b) becomes loaded with the ethanol-containing substance from step (c) as a passenger in the nanolipid particle (NLP), said ethanol-loaded nanolipid particle (NLP) carriers are sized from 20 nm-300 nm.

16. The nanolipid particle (NLP) carrier of claim 15, wherein said ethanol loaded NLP carriers formed by combining said solvent-diluted precursor stock with said aqueous-ethanol monophase remain stably sized when frozen by a commercially acceptable process for consumption while frozen.

17. The nanolipid particle (NLP) carrier of claim 15, wherein one or more lipophilic or amphipathic passenger molecules are added to the precursor stock prior to dilution with said ethanol solvent in step (b).

18. The nanolipid particle (NLP) carrier of claim 15, wherein an additional water-soluble passenger molecule is added to the aqueous solvent prior to adding the ethanol-containing substance.

19. The nanolipid particle (NLP) carrier of claim 15, wherein said precursor stock comprises phospholipids selected from the group consisting of phosphatidylcholine (PC), phosphatidylethanolamine (PE), phosphatidic acid (PA), phosphatidylinositol (PI), and mixtures thereof.

* * * * *